(12) United States Patent
Mudge

(10) Patent No.: US 9,177,223 B2
(45) Date of Patent: Nov. 3, 2015

(54) EDGE DETECTION IN IMAGES

(71) Applicant: Welch Allyn, Inc., Skaneateles Falls, NY (US)

(72) Inventor: Miguel C. Mudge, Skaneateles, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 116 days.

(21) Appl. No.: 14/154,494

(22) Filed: Jan. 14, 2014

(65) Prior Publication Data

US 2015/0199584 A1    Jul. 16, 2015

(51) Int. Cl.
| G06K 9/00 | (2006.01) |
| G06K 9/46 | (2006.01) |
| G06T 7/00 | (2006.01) |
| A61B 6/00 | (2006.01) |

(52) U.S. Cl.
CPC ............ *G06K 9/4604* (2013.01); *G06T 7/0085* (2013.01); *G06T 2207/10004* (2013.01); *G06T 2207/30016* (2013.01); *G06T 2207/30041* (2013.01)

(58) Field of Classification Search
USPC ......... 382/100, 103, 106–107, 128–134, 140, 382/162, 168, 173, 181, 194, 199, 209, 232, 382/254, 266, 274, 276, 283, 291, 305, 382/312; 359/738; 348/65; 600/407, 473
See application file for complete search history.

(56) References Cited

U.S. PATENT DOCUMENTS

| 8,913,331 | B2* | 12/2014 | Zalevsky et al. | 359/738 |
| 8,988,516 | B2* | 3/2015 | Sasamoto | 348/65 |
| 2007/0047787 | A1* | 3/2007 | Oakley et al. | 382/128 |
| 2008/0013853 | A1 | 1/2008 | Albiez et al. | |
| 2009/0180663 | A1* | 7/2009 | Stoddart et al. | 382/100 |
| 2010/0202701 | A1 | 8/2010 | Basri et al. | |
| 2011/0085703 | A1 | 4/2011 | Wiedemann et al. | |
| 2011/0238659 | A1 | 9/2011 | Chittar et al. | |
| 2012/0065518 | A1* | 3/2012 | Mangoubi et al. | 600/473 |
| 2012/0120233 | A1 | 5/2012 | Li et al. | |
| 2012/0143037 | A1 | 6/2012 | Najarian et al. | |
| 2013/0058553 | A1 | 3/2013 | Yonezawa et al. | |
| 2013/0096416 | A1 | 4/2013 | Wright | |
| 2013/0170756 | A1 | 7/2013 | Shibasaki | |
| 2014/0228668 | A1* | 8/2014 | Wakizaka et al. | 600/407 |

FOREIGN PATENT DOCUMENTS

JP    2005322043 A    11/2005

OTHER PUBLICATIONS

Martin, David R. et al., Learning to Detect Natural Image Boundaries Using Local Brightness, Color, and Texture Cues, IEEE Transactions on Pattern Analysis and Machine Intelligence, vol. 26, No. 1, Jan. 2004, 20 pgs., published by IEEE Computer Society.
Maire, Michael Randolph, Contour Detection and Image Segmentation, Fall 2009, 86 pgs.

(Continued)

*Primary Examiner* — Seyed Azarian
(74) *Attorney, Agent, or Firm* — Merchant & Gould P.C.

(57) ABSTRACT

An edge detection engine operates to scan an image to identify edges within the image. An annular aperture is used to locate the edges in the image. An output image is generated by the edge detection engine that identifies the locations of the edges found in the image.

17 Claims, 18 Drawing Sheets

(56) References Cited

OTHER PUBLICATIONS

Shetty, Prajwal, Circle Detection in Images, Summer 2011, 63 pgs.
Rad, Ali Ajdari et al., Fast Circle Detection Using Gradient Pair Vectors, Proc. VIIth Digital Image Computing: Techniques and Applications, Sun C., Talbot H., Ourselin S. and Adriaansen T. (Eds.), Dec. 10-12, 2003, Sydney, 9 pgs.
Wikipedia, Bresenham's line algorithm, May 31, 2013, 10 pgs.
Canny, John, A Computational Approach to Edge Detection, IEEE Transactions on Pattern Analysis and Machine Intelligence, vol. PAMI-8, No. 6, Nov. 1986, 20 pgs.
Wikipedia, Midpoint Circle Algorithm, May 31, 2013, 5 pgs.
Kovesi, Peter, Invariant Measures of Image Features From Phase Information, May 31, 2013, 6 pgs.
Schneider, Miya, Edge Detection, accessed Jul. 8, 2013, 4 pgs.
Wallace, Evan, Boundary Detection, accessed Jul. 8, 2013, 7 pgs.

\* cited by examiner

|   | 0 | 1 | 2 | 3 | 4 | 5 | 6 |
|---|---|---|---|---|---|---|---|
| 0 |   |   |   | +1 |   |   |   |
| 1 |   |   |   | +1 |   |   |   |
| 2 |   |   |   | +1 |   |   |   |
| 3 |   |   |   | +1 (290) |   |   |   |
| 4 |   |   |   | +1 |   |   |   |
| 5 |   |   |   | +1 |   |   |   |
| 6 |   |   |   | +1 |   |   |   |

FIG. 16

EDGE DETECTION IN IMAGES

BACKGROUND

The human eyes and brain are very good at detecting points of interest in a visual image. One way that an object is identified in an image is by the identification of edges within the image. The brain can identify edges of the object by finding points in the image where adjacent pixels exhibit a distinct contrast. Numerous edges in the image combine to create an overall shape. The shape in the image is then compared with the shapes of known objects. If the shape is sufficiently similar to a known object, the brain can identify the object in the image.

Computers cannot process images in the same way as the human brain. Often images lack sufficient detail or contrast for a computer to be able to detect relevant features. Even the fundamental step of identifying the location of edges within an image can be challenging to perform with a computer. Without an adequate identification of the locations of edges in an image, the computer is unable to perform subsequent operations, such as identifying objects or other points of interest within the image.

SUMMARY

In general terms, this disclosure is directed to edge detection in images. In one possible configuration and by non-limiting example, the edge detection involves scanning the image using an annular aperture. Various aspects are described in this disclosure, which include, but are not limited to, the following aspects.

One aspect is a method of detecting edges within a digital image, the method comprising: processing at least a portion of the digital image, using a computing device, in a pixel-by-pixel manner including at an analysis point in the digital image, by: identifying pixels surrounding the analysis point; identifying a location of a bisection that divides the pixels surrounding the analysis point into two halves; determining an angle of the bisection that maximizes a difference in intensities of the pixels between the two halves; and determining that an edge is present in the digital image at the angle of the bisection.

Another aspect is an edge detection system comprising: a computing device comprising: a processing device; and a computer readable storage device storing data instructions that, when executed by the processing device generates an edge detection engine comprising: an annular aperture generator that operates to generate an annular aperture using a circle drawing algorithm; a line generator that generates lines representative of a set of bisectors of the annular aperture; an image scanning engine that utilizes the annular aperture as a mask to scan a digital image and identify edges within the digital image; and an output data generator that utilizes the lines to represent the edges in the output image.

A further aspect is a medical instrument comprising: an image capture device operable to capture an input image; and a computing device including an edge detection engine, the edge detection engine operable to process the input image to detect edges within the input image by processing the image using an annular aperture mask.

BRIEF DESCRIPTION OF THE DRAWINGS

FIG. 16 is a schematic diagram illustrating an example operation to draw a line in the output image.

DETAILED DESCRIPTION

Figure 1:
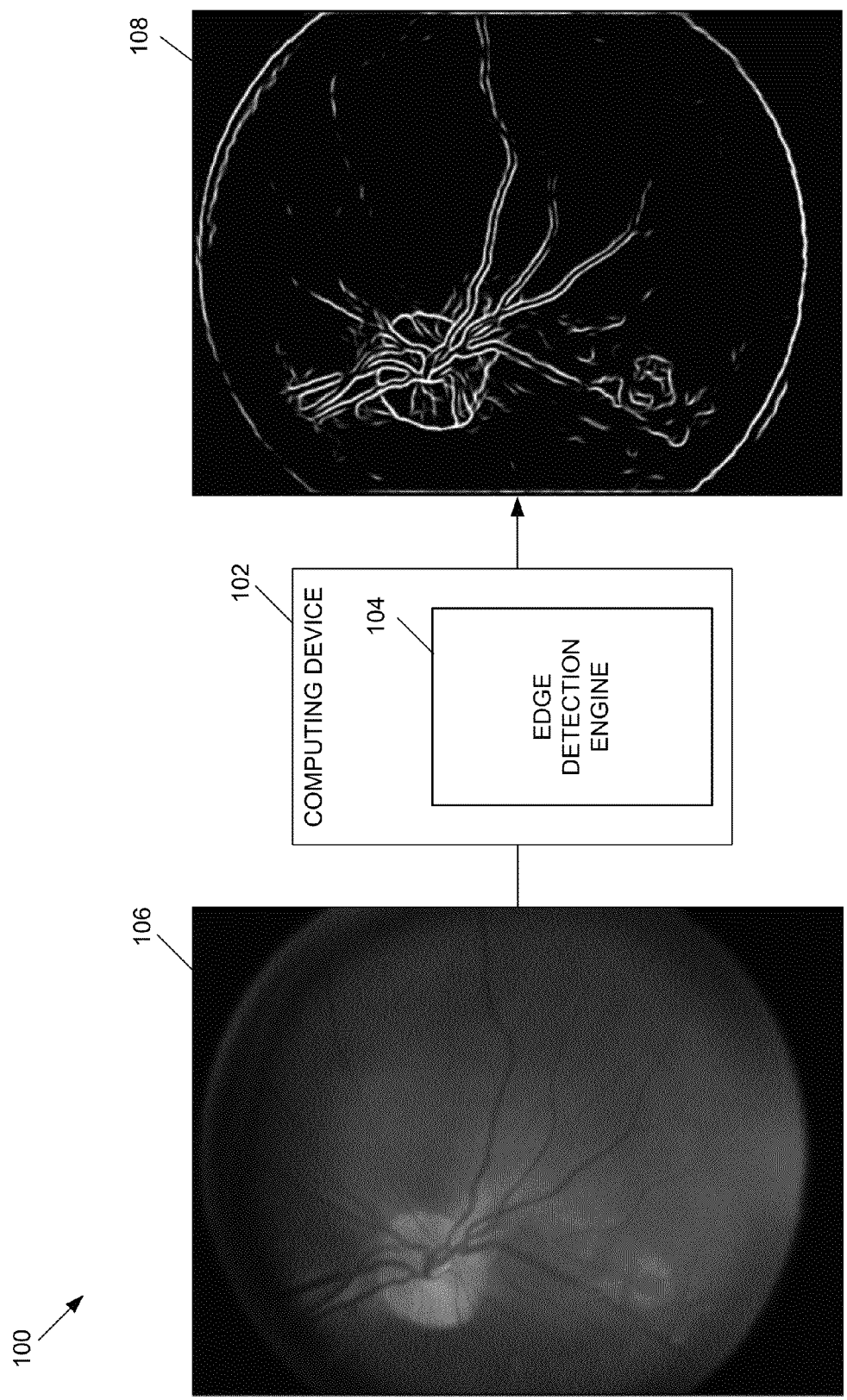
FIG. 1 is a schematic diagram illustrating an example of an edge detection system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a schematic diagram illustrating an example of an edge detection system 100. In this example, the edge detection system 100 includes a computing device 102 that executes an edge detection engine 104. Also shown are an input image 106 and an output image 108.

Figure 17:
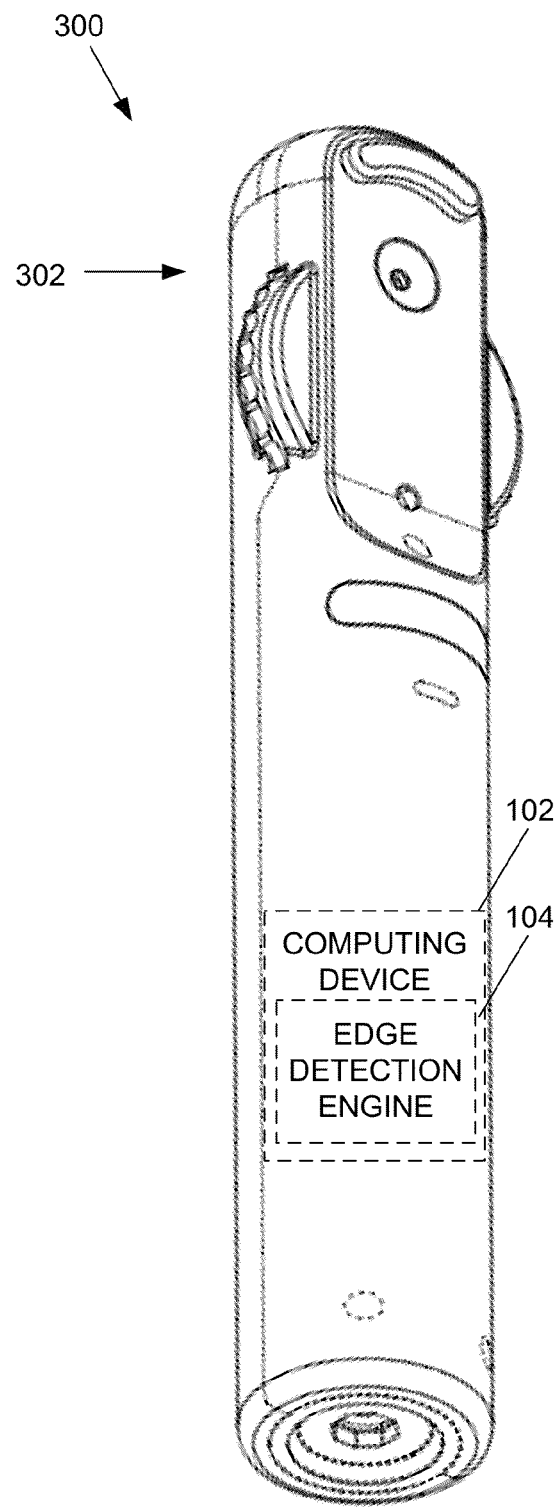
FIG. 17 is a perspective view of an example instrument in which aspects of the present disclosure can be implemented.

The edge detection system 100 can be implemented in multiple different forms. In one embodiment, for example, the edge detection system 100 is part of an instrument, such as a medical instrument. One example of a medical instrument is an ophthalmoscope, such as shown in FIG. 17. Another example of a medical instrument is a colposcope. In these examples, the computing device 102 can be part of the instrument, for example. In another embodiment, the edge detection system 100 is implemented in a computing device 102 separate and distinct from an instrument. For example, in some embodiments the computing device 102 is a computer or part of a computer.

The computing device 102 typically includes at least a processing device and a computer-readable storage device. In some embodiments the computer-readable storage device stores data instructions, which when executed by the processing device, causes the processing device to perform one or more of the functions, methods, or operations, of the edge detection engine 104 described herein. An example of a computing device 102 is illustrated and described in more detail with reference to FIG. 18.

The edge detection engine 104 operates to detect edges in an input image 106. In some embodiments the results of the edge detection are output in the form of an output image 108, which contains data identifying the locations of the edges detected in the input image 106.

In some embodiments, the input image 106 is captured by an instrument, such as a medical instrument. In the example shown in FIG. 1, the input image 106 is an image of an eye captured from an ophthalmoscope. The input image 106 can also come from other sources. Typically the input image 106 is captured by an image capture device, such as a charge-coupled device or a complementary metal-oxide-semiconductor active pixel sensor.

In some embodiments the input image 106 is stored in the computer-readable storage device in the form of an image file. The image can be encoded according to one or more of various image file formats. One example of a suitable image file format is the Joint Photograph Expert Group (JPEG) file format. Other examples of image file formats include exchangeable image file format (EXIF), tagged image file format (TIFF), raw image format (RAW), portable network graphics (PNG) format, graphics interchange format (GIF), bitmap file format (BMP), and portable bitmap (PBM) format. Other embodiments utilize other image file formats. The input data could also be provided in a non-image file format, such as utilizing another data format to convey the image data.

In some embodiments each pixel of the input image 106 is encoded in multiple color channels, such as red, green, and blue color channels. The color channels include an intensity value that indicates the relative contribution of that color to the pixel color. In other words, each pixel is represented by an intensity value within each color channel. The intensity values typically range from 0 to 255, for example. So, for example, a pixel that is primarily red will have a large intensity value in the red color channel and smaller intensity values in the blue and green color channels. A white pixel will have approximately equal intensities in all three color channels.

In some embodiments only one color channel of the input image 106 is used by the edge detection engine 104. For example, to evaluate red features (e.g., oxygenated blood) within the eye, the red color channel of the input image 106 can be used. To evaluate blue features (e.g., a vein), the blue color channel of the input image 106 can be used. In other embodiments, two or more of the color channels are used. Further, some embodiments involve a color space transformation. Such a transformation can be used to evaluate other colors, such as cyan, magenta, and/or yellow, for example. Hue, saturation, and/or brightness are used in some embodiments.

The output image 108 is generated by the edge detection engine 104, and includes data that identifies the locations of edges detected in the input image 106. In some embodiments the pixels in the output image 108 include intensity values. The more distinct the edge is in the input image 106, the larger the intensity value will be at the corresponding point in the input image 106. In some embodiments the output image 108 is also encoded in an image file format, such as the JPEG file format, or another format.

Figure 2:
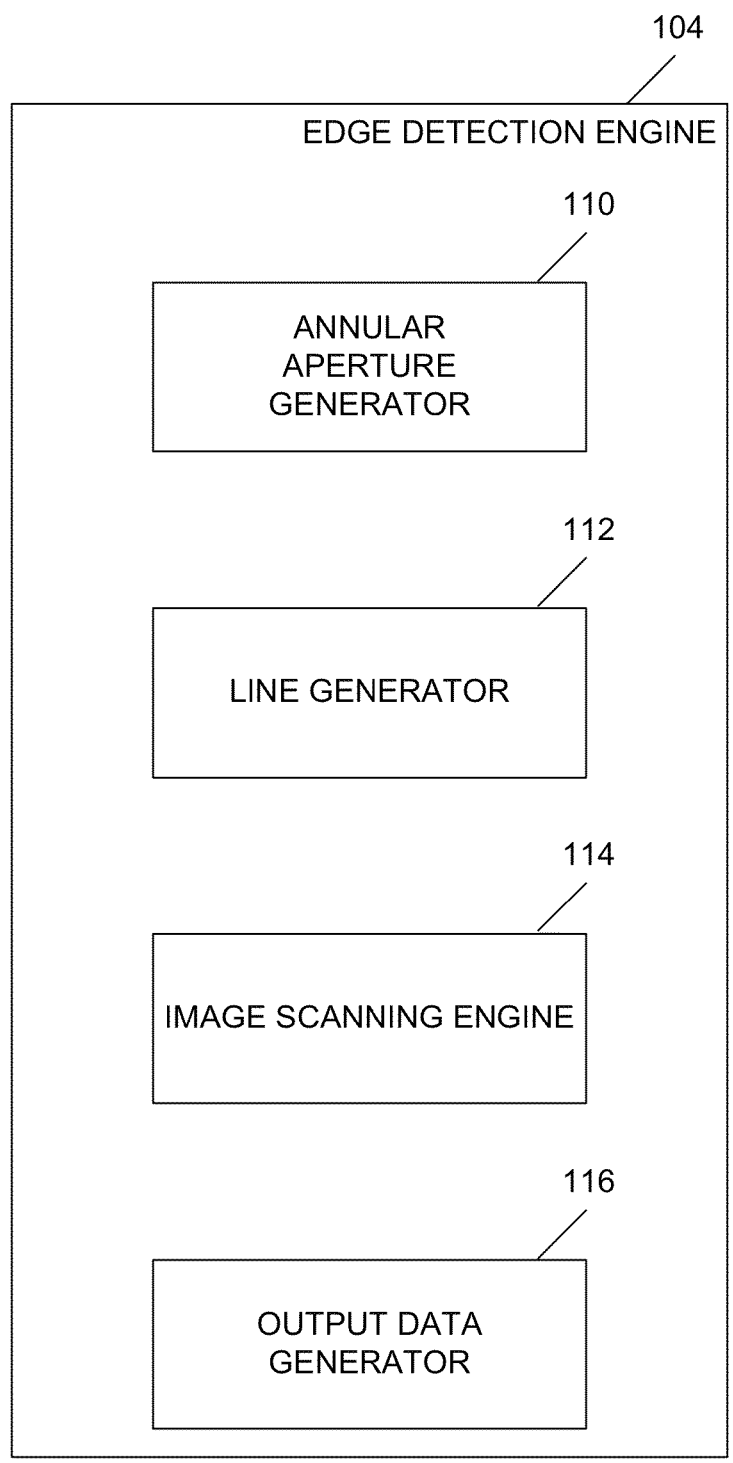
FIG. 2 is a schematic block diagram illustrating an example of an edge detection engine of the edge detection system shown in FIG. 1.

FIG. 2 is a schematic block diagram illustrating an example of the edge detection engine 104. In this example, the edge detection engine 104 includes an annular aperture generator 110, a line generator 112, an image scanning engine 114, and an output data generator 116.

The annular aperture generator 110 operates to define an annular aperture. In some embodiments the edge detection engine 104 utilizes the annular aperture to scan the input image 106 to identify edges in the input image, as discussed in further detail below. An example of the annular aperture generator 110 is discussed in further detail herein with reference to FIGS. 3-4.

The line generator 112 operates to define a set of lines. More specifically, in some embodiments the line generator 112 determines all of the possible ways that the annular aperture (generated by the annular aperture generator 110) can be bisected, and generates a set of lines defining each of the possible bisections. In another possible embodiment, the line generator 112 is operated to generate specific lines as needed. An example of the line generator 112 is discussed in further detail with reference to FIGS. 5-6.

The image scanning engine 114 operates to scan the input image 106, shown in FIG. 1, to detect edges in the input image 106. An example of the image scanning engine 114 is discussed in further detail with reference to FIGS. 7-12.

The output data generator 116 operates to generate an output of the edge detection engine 104. In some embodiments the output data generator 116 generates the output image 108, shown in FIG. 1. The output data generator 116 is discussed in further detail with reference to FIGS. 13-16.

Figure 3:
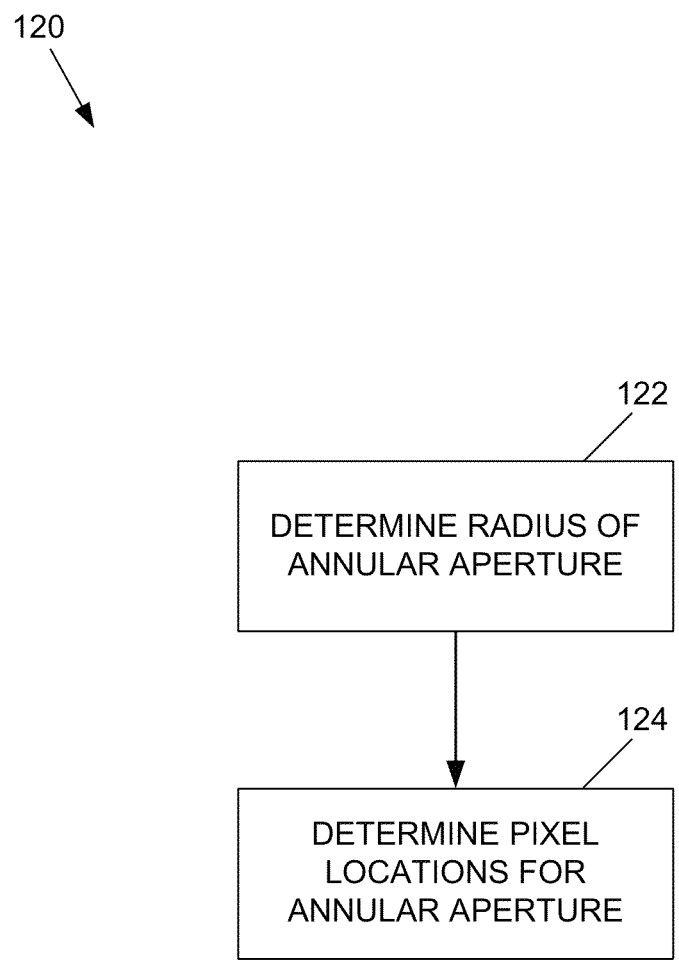
FIG. 3 is a flow chart illustrating an example method of generating an annular aperture.
Figure 4:
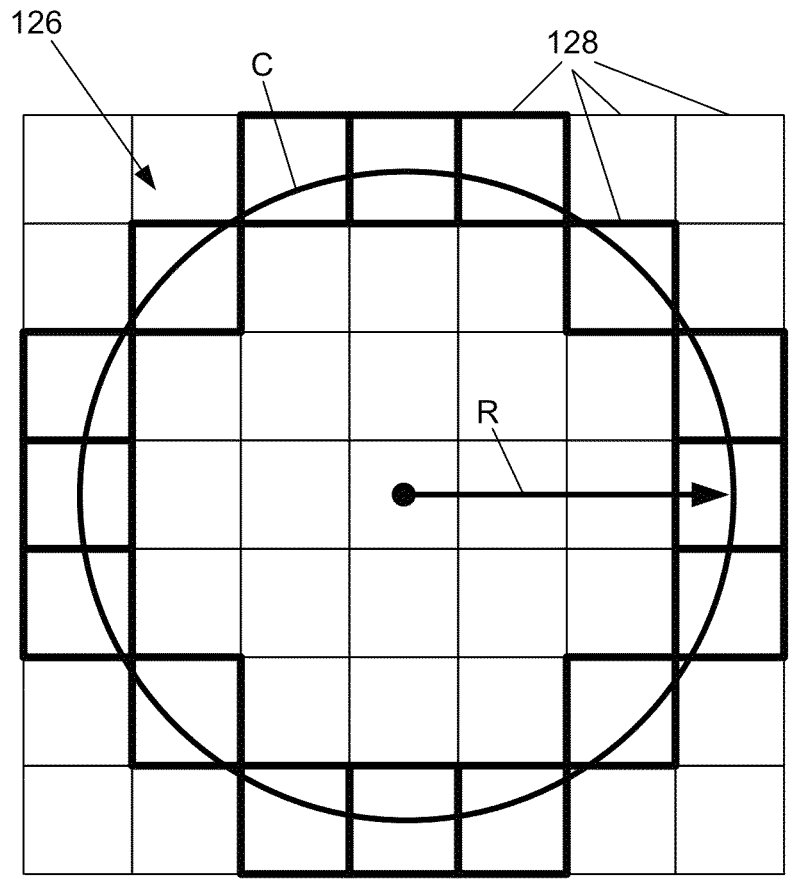
FIG. 4 is a schematic diagram illustrating an example of the annular aperture.

FIGS. 3-4 illustrate examples of the annular aperture generator 110, shown in FIG. 2.

FIG. 3 is a flow chart illustrating an example method 120 of generating an annular aperture. In some embodiments the method 120 is performed by the annular aperture generator 110, shown in FIG. 2. In this example, the method 120 includes an operation 122 and an operation 124.

The operation 122 is performed to determine a radius of an annular aperture to be generated. In some embodiments the radius is of a predetermined size. In other embodiments the radius is a selectable parameter. For example, in some embodiments the annular aperture generator 110 prompts a user to enter a desired radius. The optimum radius dimension will typically depend on multiple factors, such as the resolution of the input image 106, the size and complexity of the features of interest in the input image 106, and the level of noise (e.g., unimportant details) in the input image 106. As one example, the radius is in a range from about 5 pixels to about 25 pixels. In some embodiments the radius is about 10 pixels.

Some embodiments utilize other parameters. For example, another possible parameter is the thickness of the annular aperture. In other embodiments, the annular aperture has a predetermined thickness, such as a thickness of one pixel.

The operation 124 is performed to generate the annular aperture. Because of the grid-like arrangement of pixels in an image, a perfect circular shape cannot be drawn using pixels. Accordingly, in some embodiments the operation 124 determines pixel locations for the annular aperture that approximate a circular shape. An example of operation 124 is illustrated in FIG. 4.

FIG. 4 is a schematic diagram illustrating an example of an annular aperture 126. A plurality of pixels 128 is also shown. The annular aperture 126 is formed within the plurality of pixels 128, in some embodiments.

In this example, the desired annular aperture 126 has a radius R and is in the shape of a circle C.

Because the annular aperture 126 needs to be defined within the plurality of pixels 128, which are arranged in a grid-like configuration, it is not possible for a perfectly circular annular aperture 126 to be generated. As a result, the operation 124 (shown in FIG. 3) is performed to determine pixel locations for the annular aperture that approximate the shape of the circle C.

In some embodiments, the pixel locations are determined using a circle drawing algorithm. One example of a circle drawing algorithm is the midpoint circle algorithm, also known as the Bresenham's circle algorithm. Other embodiments utilize other circle drawing algorithms.

Using the circle drawing algorithm with a known radius R (e.g., a radius of 7), the annular aperture 126 is generated as represented by the pixels shown in bold lines in FIG. 4. The annular aperture 126 has a shape that approximates the shape of the circle C and has a radius R and a thickness of one pixel.

The annular aperture 126 generated by the annular aperture generator 110 (FIG. 2) is stored for subsequent use.

Figure 5:
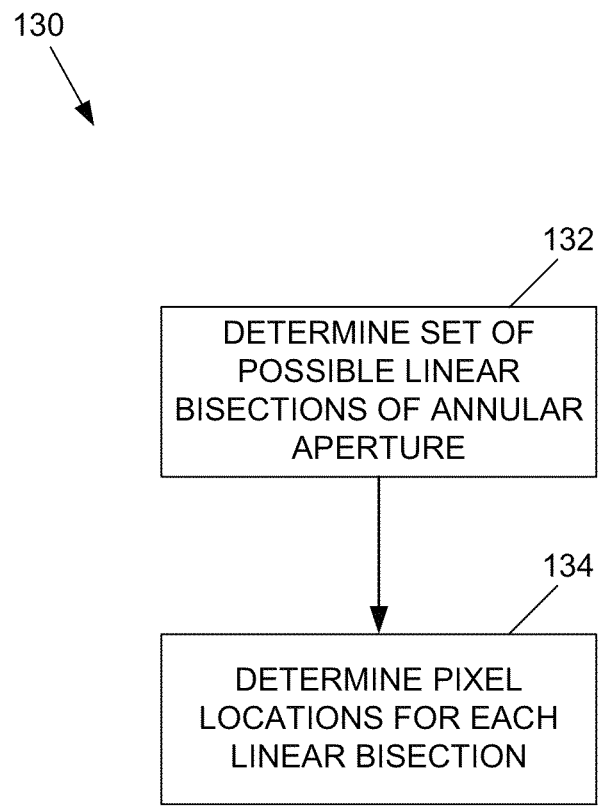
FIG. 5 is a flow chart illustrating an example method of generating a plurality of lines representing a set of possible bisections of the annular aperture shown in FIG. 4.

FIG. 5 is a flow chart illustrating an example method 130 of generating a plurality of lines representing the set of possible bisections of the annular aperture shown in FIG. 4. In this example the method 130 includes operations 132 and 134. In some embodiments the operations 132 and 134 are performed by the line generator 112, shown in FIG. 104.

The operation 132 is performed to determine a set of possible linear bisections of an annular aperture. An example of the annular aperture is shown in FIG. 4.

Before searching through the image for possible edges, the operation 132 can be performed to identify the possible shapes of those edges. In other words, the edge might be a vertical line extending from the top to the bottom of the annular aperture, or it could be a horizontal line extending from the left to the right of the aperture. The edge could also be present at some other angle. Because the digital image has a limited number of pixels, the quantity of lines that can be formed within the annular aperture is limited. In some embodiments, the lines are determined by starting at a first pixel of the annular aperture 126 and identifying a line that can be drawn from that point to the corresponding point directly opposite that point. The process is then repeated consecutively for each point around the annular aperture until all possible angles have been evaluated. An example of the set of possible linear bisections is shown in FIG. 6.

The operation 134 is performed to determine pixel locations for each linear bisection. Stated another way, the operation 134 is performed to draw each of the lines between opposing points of the annular aperture 126.

Because of the grid-like arrangement of the pixels, straight lines can only be drawn vertically and horizontally in the pixels. A straight line having an angle that is not vertical or horizontal cannot be perfectly represented in the pixels. Therefore, in some embodiments the operation 134 involves the use of a line drawing algorithm. One example of a line drawing algorithm is the Bresenham's line algorithm. The line drawing algorithm determines a set of pixels that form an approximation to a perfect line extending between two opposing points of the annular aperture.

Figure 6:
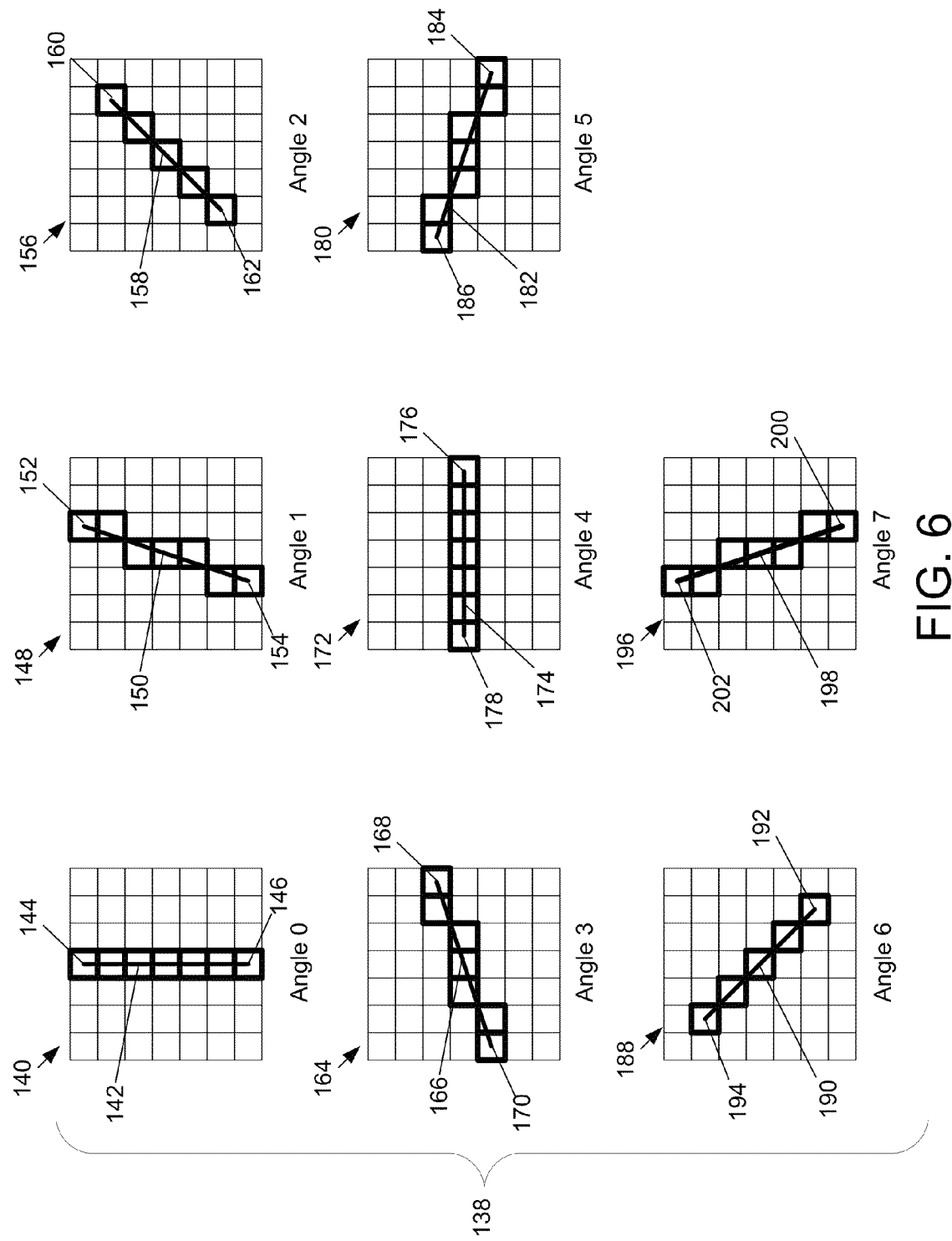
FIG. 6 is a schematic diagram illustrating an example set of linear bisections for the example annular aperture shown in FIG. 4.

FIG. 6 is a schematic diagram illustrating an example set 138 of linear bisections for the example annular aperture 126 shown in FIG. 4.

In this example, the set 138 of linear bisections are formed by identifying all straight lines that can bisect the annular aperture 126 (FIG. 4) at various angles. One way to do this is to begin with a starting pixel of the annular aperture 126, such as the pixel 144, draw the linear bisector extending from this pixel to the corresponding pixel on the opposite side of the annular aperture 126, and then consecutively rotate through the adjacent pixels of the annular aperture 126 in the same manner until all possible bisections have been identified. The number of possible bisections varies depending on the pixel size of the annular aperture 126. In this example, the annular aperture has a diameter of seven pixels, and eight possible bisections, as shown.

Each linear bisection can be identified by an angle of the bisection with respect to a starting location. In this example the angles are identified by a number of pixels around the annular aperture, such that angle 0 is the angle of a linear bisection passing through a first pixel (144) of the annular aperture, angle 1 is the angle of a linear bisection passing through a second pixel (152) of the annular aperture, and so on.

Although it is possible to convert the angles to degrees, the conversion would require additional processing steps that are unnecessary. As one example, however, the annular aperture can be bisected by eight different lines, such that the angle between each adjacent pixel of the annular aperture is 22.5 degrees (180/8=22.5). Note that the linear bisections from 0 to 180 degrees are the same as the linear bisections from 180 to 360 degrees, such that the computation of one set of the linear bisections is adequate to address all possible linear bisections of the annular aperture.

The first linear bisection 140 in the set 138, with an angle 0 (0 degrees), is the approximation of a line 142 extending vertically across the annular aperture. The linear bisection extends from pixel 144 to the corresponding opposite pixel 146. The linear bisection 140 includes seven pixels from pixel 144 to pixel 146.

The next linear bisection 148, with an angle 1 (22.5 degrees), is the approximation of a line 150 extending from the next pixel 152 in the clockwise direction from the first pixel 144, to the corresponding opposite pixel 154. In this example it can be seen how the line 150 cannot be perfectly represented in the pixels, and therefore a set of seven pixels extending from pixel 152 to pixel 154 are selected to best approximate the line 150.

The next linear bisection 156, with an angle 2 (45 degrees), is the approximation of a line 158. The linear bisection includes seven pixels extending from pixel 160 to pixel 162.

The linear bisection 164 has an angle A3 (67.5 degrees), and is the approximation of a line 166. The linear bisection extends from a pixel 168 to a pixel 170.

The linear bisection 172 is an approximation of the horizontal line 174 having an angle 4 (90 degrees), which extends from pixel 176 to pixel 178.

The next linear bisection 180 has an angle A5 (112.5 degrees), and is the approximation of a line 182. The linear bisection 180 extends from pixel 184 to pixel 186.

The linear bisection 188 has an angle A6 (135 degrees), and is the approximation of a line 190. The linear bisection 188 extends from pixel 192 to pixel 194.

At angle A7 (157.5 degrees) is the linear bisection 196 that approximates the line 198. The linear bisection extends from pixel 200 to pixel 202.

Advancing to the next pixel around the annular aperture arrives at pixel 146, and the linear bisection from pixel 146 is the same as the line 140 at angle 0. Therefore, all linear bisections have been identified for the example annular aperture 126, shown in FIG. 4. Larger annular apertures will have a larger quantity of linear bisections, while smaller annular apertures will have a smaller quantity of linear bisections.

In some embodiments the set 138 of linear bisections is stored in a computer readable storage device for subsequent use.

Figure 7:
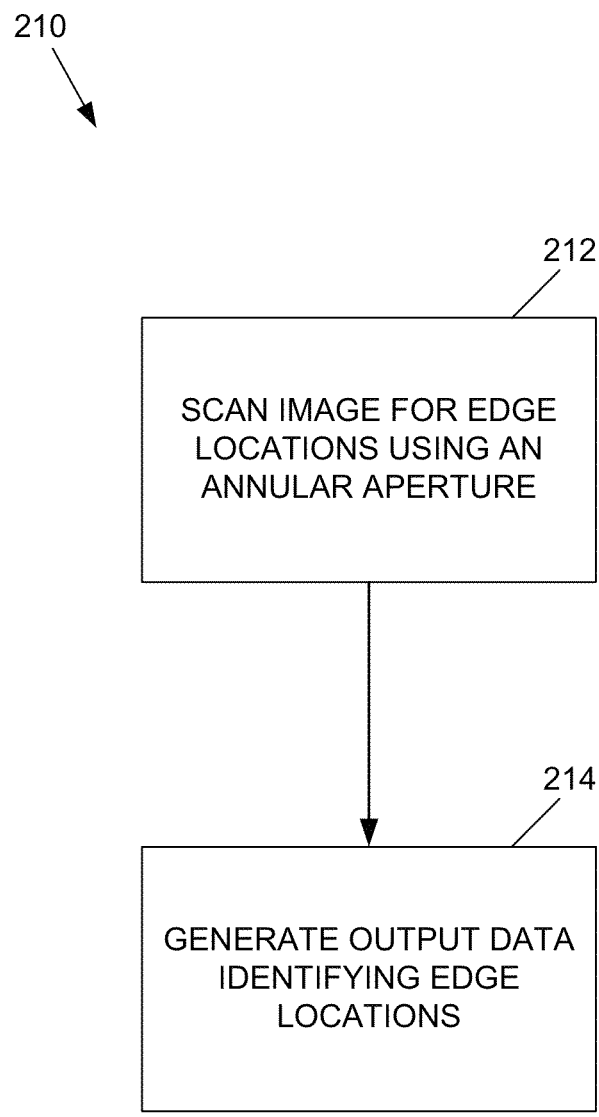
FIG. 7 is a flow chart illustrating an example method of scanning an image using the annular aperture shown in FIG. 4.

FIG. 7 is a flow chart illustrating an example method 210 of scanning an image using an annular aperture. In this example, the method 210 includes operations 212 and 214. In some embodiments the operations 212 and 214 are performed by an image scanning engine 114, shown in FIG. 2.

The operation 212 is performed to scan an image 106 (FIG. 1) for edge locations using an annular aperture. An example of operation 212 is illustrated and described in more detail with reference to FIGS. 8-12.

The operation 214 is performed to generate an output image 108 (FIG. 1) identifying the edge locations. An example of operation 214 is illustrated and described in more detail with reference to FIGS. 13-16.

Figure 8:
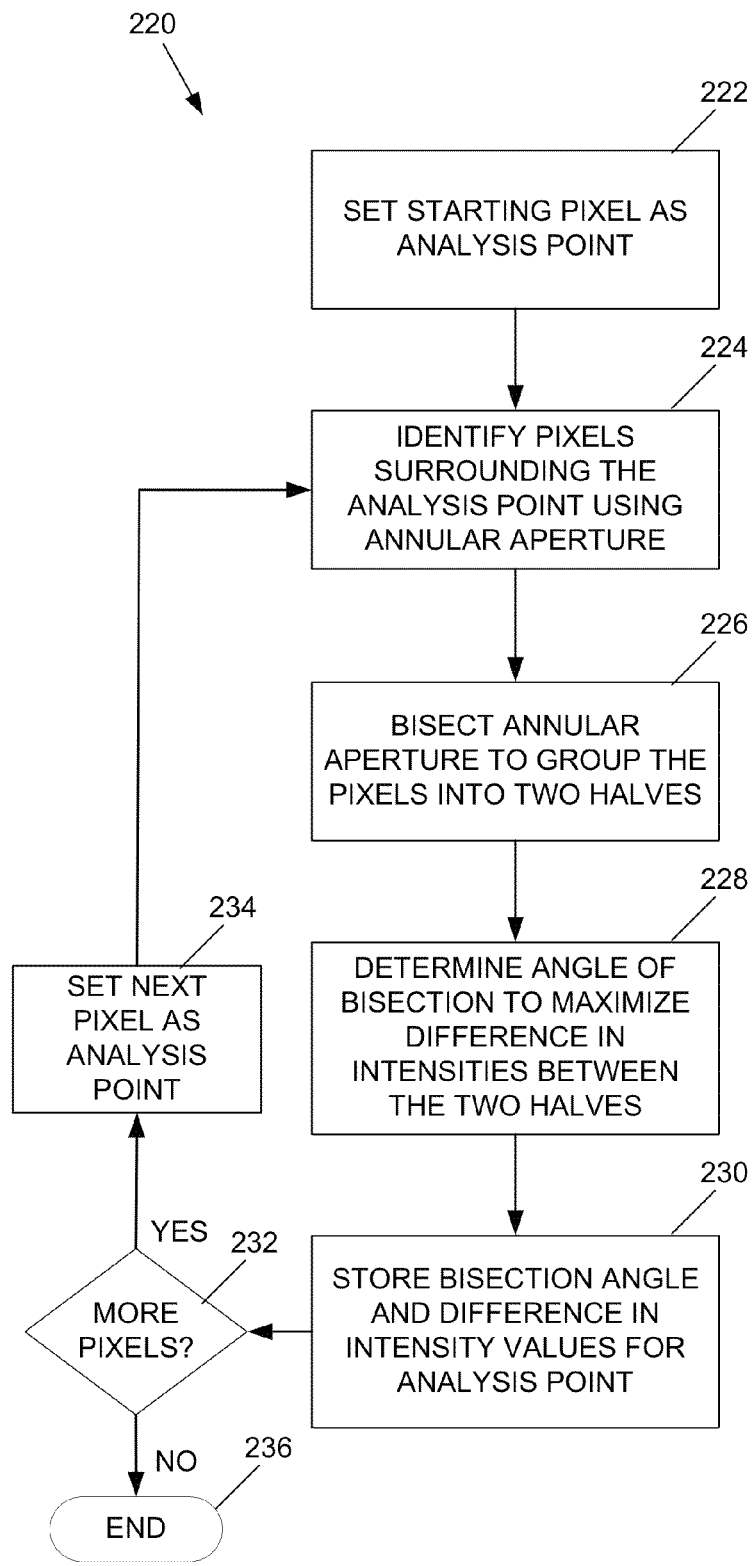
FIG. 8 is a flow chart illustrating an example method of scanning an image for edge locations using the annular aperture shown in FIG. 4.

FIG. 8 is a flow chart illustrating an example method 220 of scanning an image for edge locations using an annular aperture. FIG. 8 also illustrates an example of the operation 212, shown in FIG. 7. In this example, the method 220 includes operations 222, 224, 226, 228, 230, 232, 234, and 236.

The method 220 is performed to scan an input image, such as the image 106, shown in FIG. 1, to identify edges within the image 106. As described herein, in some embodiments the method 220 involves scanning only a single color channel of the input image 106. For example, the red color channel can be evaluated. Within the red color channel, each pixel of the image 106 is represented by an intensity value. The intensity value can be a value between 0 and 255, for example. The intensity value indicates the brightness of the color associated with the color channel (e.g., red) in the pixel.

The operation 222 is performed to determine a starting pixel, and to begin the scanning and analysis of the image at that point. For example, the starting pixel can be the upper left pixel of the image.

A problem with edge or corner pixels, however, is that evaluation of such pixels requires that the annular aperture 126 (FIG. 4) be positioned such that the annular aperture 126 extends outside of the bounds of the image. In such a case, it is desirable to know what the background color is in the image. For example, if it is known that the background is black, the evaluation can proceed by using a default intensity value corresponding with the background color (e.g., an intensity of zero, representing a dark pixel).

Figure 9:
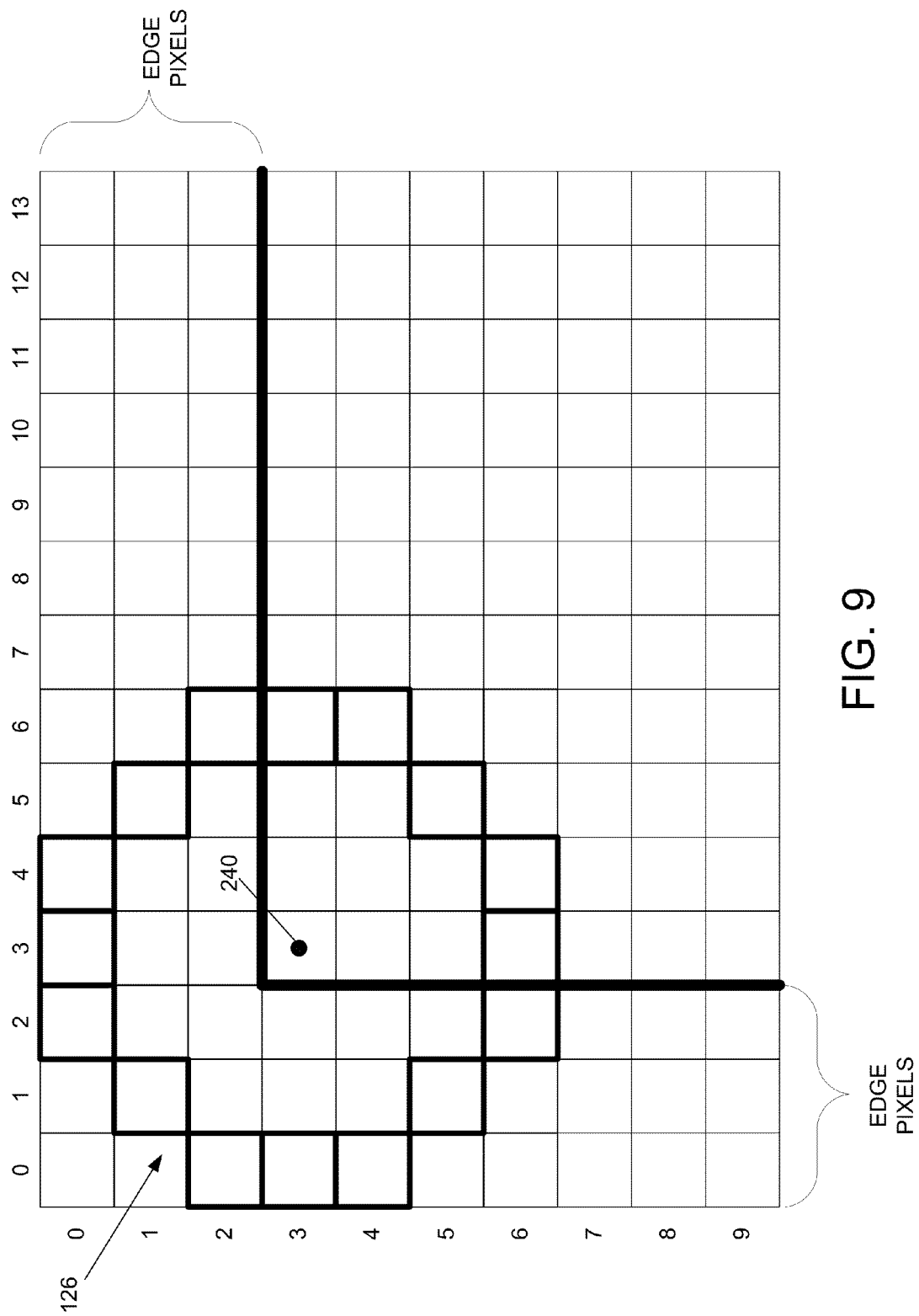
FIG. 9 is a schematic diagram illustrating an example of a starting pixel of an input image, and also showing an example of pixels of an image that are within the annular aperture.

Alternatively, pixels that are less than the radius of the annular aperture 126 (FIG. 4) away from the edge are omitted from processing in method 220. For an annular aperture having a diameter of 7 pixels, for example, the starting pixel can be the pixel that is four pixels down and four pixels to the right of the upper left pixel. An example is shown in FIG. 9. Various other starting points could also be used in other embodiments.

Once the starting point has been determined and set as the first analysis point in the image 106, the operation 224 is performed to identify pixels surrounding the analysis point using the annular aperture 126 (FIG. 4). To do so, the annular aperture 126 is used as a mask layer to identify only those pixels in the image 106 that are within the annular aperture 126 when the annular aperture 126 is centered on the analysis point. An example is shown in FIG. 9.

Figure 10:
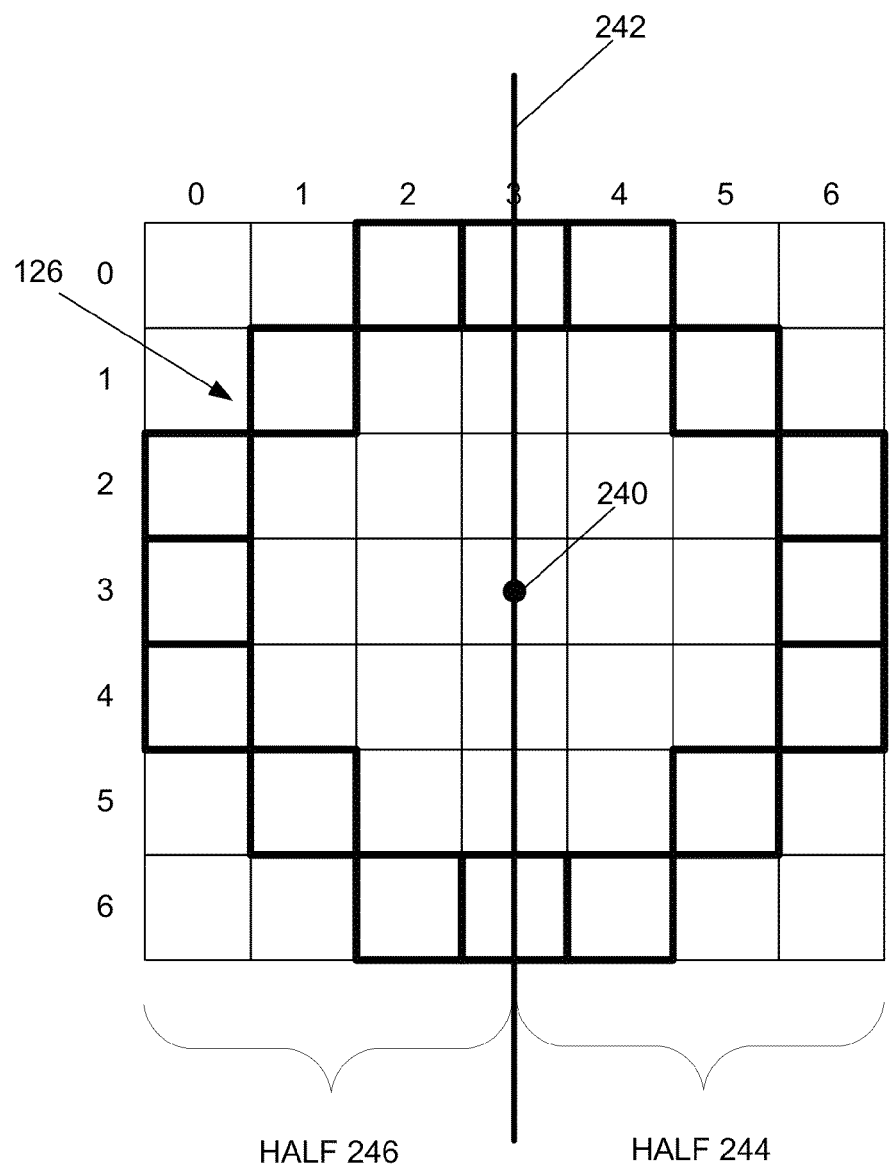
FIG. 10 is a schematic diagram illustrating an operating in which the annular aperture is bisected along a bisection line to group the pixels within the annular aperture into two halves.

The operation 226 is performed to bisect the annular aperture 126 to group the pixels into two halves. An example of operation 226 is shown in FIG. 10.

The operation 228 is performed to determine an angle of the bisection that maximizes a difference in intensities between the two halves. To do so, the intensity values for each pixel within a first half of the annular aperture 126 are added together, and the intensity values for each pixel within the second half of the annular aperture 126 are also added together. The combined intensity value of the first half is then compared with the combined intensity value of the second half to determine a difference between the intensity values.

Figure 11:
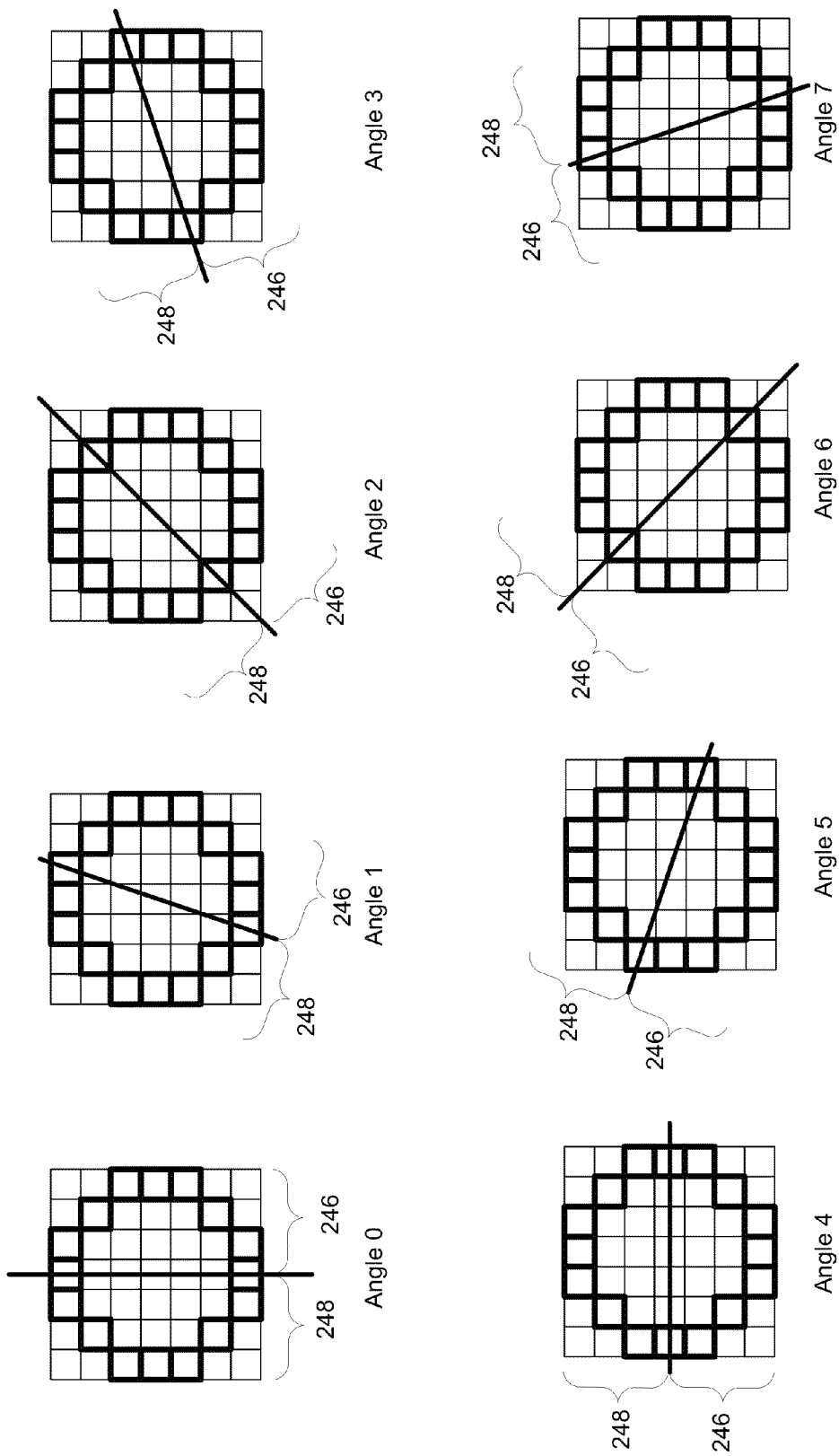
FIG. 11 is a schematic diagram illustrating an example operation that determines an angle of the bisection that maximizes a difference in intensities between the two halves.

The same process is repeated for each possible bisection of the annular aperture 126, and the differences between the intensity values are determined for each possible bisection. An example is illustrated in FIG. 11.

If a large difference in the intensity values is found for a given bisection, the difference indicates the likely presence of an edge within the image 106 at or near the location of the analysis point.

The operation 228 identifies the bisection angle that results in the greatest difference in the intensity value between the two halves.

Figure 12:
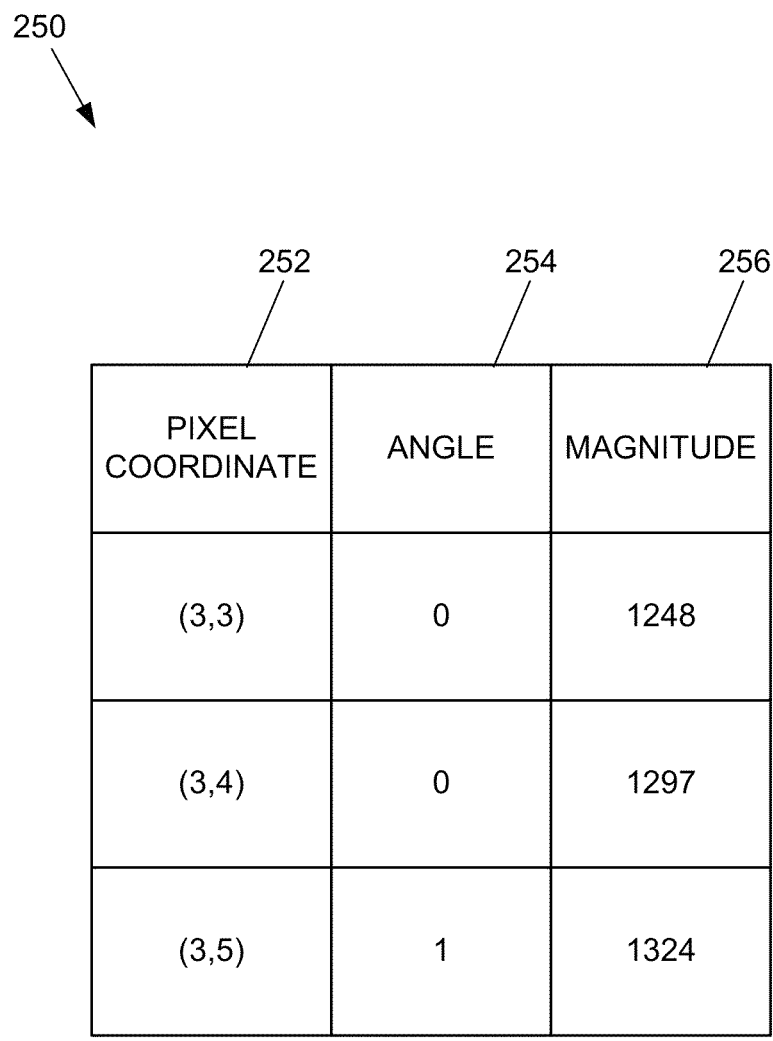
FIG. 12 illustrates an example of an angle and magnitude map.

In operation 230, the angle that results in the greatest difference is then stored in a computer readable storage device for the analysis point, along with the intensity value difference. The different in the intensity values between the two halves is sometimes referred to herein as a magnitude. In some embodiments the angle and magnitude are stored in an angle and intensity map. An example of an angle and intensity map is shown in FIG. 12.

Once the angle and the magnitude have been computed and stored for the analysis point, operation 232 determines whether there are additional pixels that need to be analyzed. If so, operation 234 sets the next pixel as the analysis point and repeats operations 224, 226, 228, 230, and 232 accordingly. Otherwise the method 220 ends at operation 236.

FIG. 9 is a schematic diagram illustrating an example of a starting pixel of an input image 106, and also showing an example of the pixels of the image that are within the annular aperture 126. Only an upper left portion of the image 106 is represented in FIG. 9.

In this example, the annular aperture has a diameter of seven pixels. As a result, any pixels that are located less than the radius (3.5 pixels) of the annular aperture away from the edge of the image are designated as edge pixels. If the annular aperture were centered on an edge pixel, a portion of the annular aperture would extend outside of the bounds of the image. In some embodiments the scanning of the image involves the use of interior pixels that are greater than the radius of the annular aperture 126 away from the bounds of the image.

In some embodiments each pixel of the image 106 is represented by a coordinate value of (X,Y), where X is the horizontal number of pixels from the left side of the image and Y is the vertical number of pixels from the top of the image. The upper left pixel has a coordinate (0,0).

In this example, the pixel (3,3) is selected as the starting pixel, and is therefore set as the first analysis point 240.

The annular aperture 126 is then used to identify a set of pixels surrounding the analysis point that are within the annular aperture 126. In FIG. 9 the pixels within the annular aperture are represented with bold lines.

FIG. 10 is a schematic diagram illustrating an example of operation 226, shown in FIG. 8, during which the annular aperture 126 is bisected along a bisection line 242 to group the pixels within the annular aperture 126 into two halves 244 and 246.

The annular aperture 126 is bisected along a bisection line 242. The example shown in FIG. 10 illustrates a vertical bisection line 242. The vertical bisection line 242 divides the annular aperture 126 into two halves 244 and 246, permitting the pixels within the annular aperture 126 to be grouped according to the corresponding halves 244 and 246.

FIG. 11 is a schematic diagram illustrating an example of operation 248, shown in FIG. 8, which determines an angle of the bisection that maximizes a difference in intensities between the two halves 246 and 248.

In this example, the annular aperture is bisected along all possible bisection lines from the angle 0 to the angle 7. For each bisection, a sum of the intensities of the pixels in the half 246 is compared with a sum of the intensities of the pixels in the half 248, and a difference between the intensity values is computed. The bisection angle that results in the greatest difference between the two halves is then identified.

FIG. 12 illustrates an example of an angle and magnitude map 250, such as generated by the method 220, shown in FIG. 8. Only a representative portion of an example angle and magnitude map 250 is shown in FIG. 12.

In this example, the angle and magnitude map 250 includes pixel coordinates 252, angles 254, and magnitudes 256.

The pixel coordinate 252 identifies an analysis point of the image.

The angle 254 identifies the bisection angle that was found to result in the greatest difference in intensities between the two halves of the annular aperture for the analysis point identified by the pixel coordinate 252.

The magnitude 256 identifies the difference in intensities that was computed at the angle 254 for the analysis point identified by the pixel coordinate 252.

Figure 13:
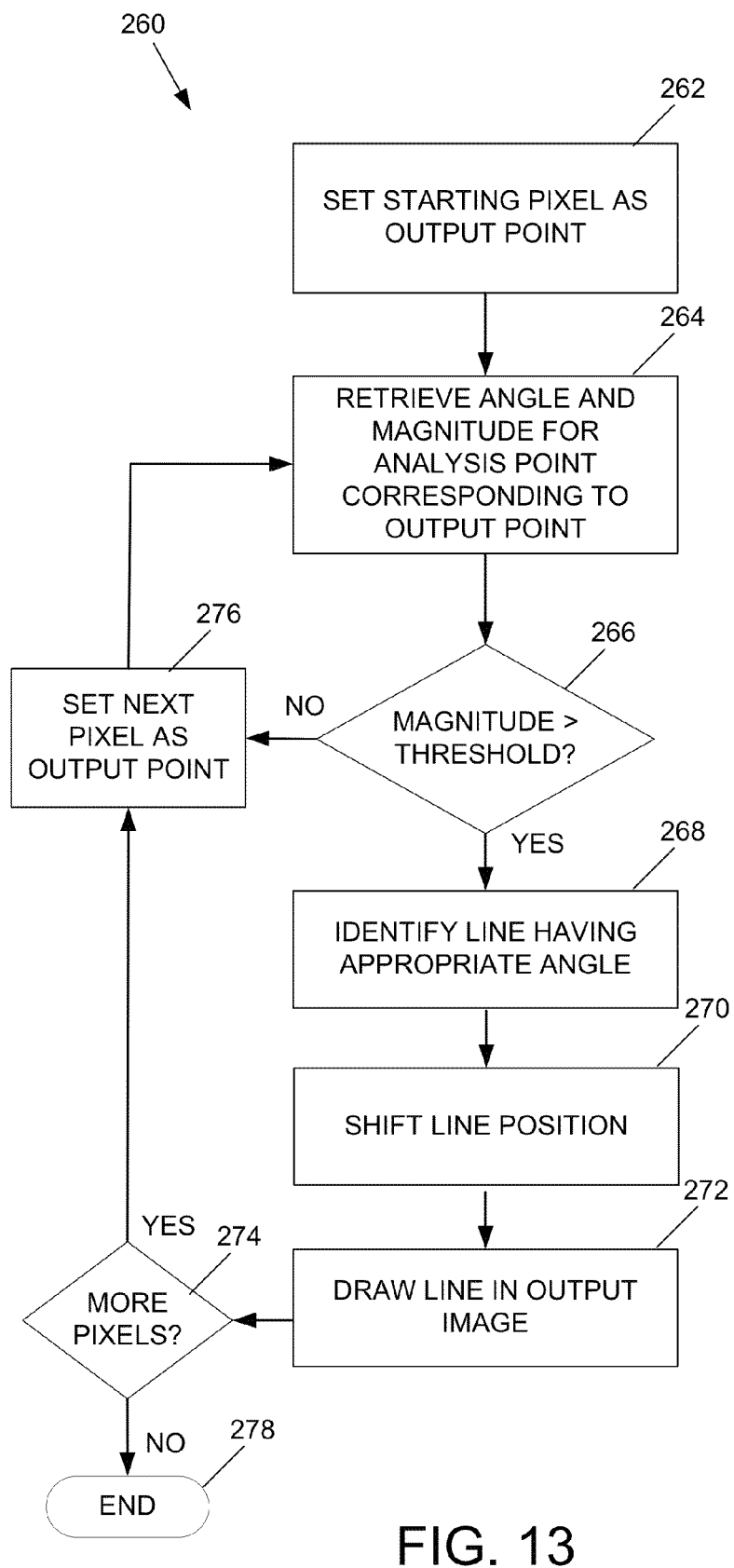
FIG. 13 is a flow chart illustrating an example method of generating an output image identifying the locations of edges in an input image.

FIG. 13 is a flow chart illustrating an example method 260 of generating an output image 108 (shown in FIG. 1) identifying the locations of edges in an input image 106 (also shown in FIG. 1). FIG. 13 also illustrates an example of the operations performed by some embodiments of the output data generator 116, shown in FIG. 2. In this example the method 260 includes operations 262, 264, 266, 268, 270, 272, 274, 276, and 278.

The method 260 is performed to generate the output image 108, which identifies edges within the input image 106. To do so, the output image 108 is processed on a pixel-by-pixel basis, just as the input image was processed on a pixel-by-pixel basis (such as in the example method 220, shown in FIG. 8). For each analysis point of the input image 106, a corresponding output point of the output image is processed by the method 260.

The operation 262 begins by setting a starting pixel as the first output point. In some embodiments the same starting point is used in operation 262 as in the operation 222 shown in FIGS. 8 and 9, except that the output point identifies the corresponding pixel of the output image 108 rather than the input image 106. Typically the same pixel coordinates are used to identify the pixels in the input and output images 106 and 108 so that a coordinate of an output point of the output image 108 corresponds to the same coordinate of the analysis point of the input image 106.

The operation 264 is performed to retrieve an angle and magnitude for the analysis point corresponding to the output point from the angle and magnitude map 250 (FIG. 12).

The operation 266 is then performed to determine whether the magnitude exceeds a threshold value. If the magnitude does not exceed the threshold, it is determined that the input image 106 does not contain a sufficiently distinct edge at or near to the output point, and therefore method 260 continues with operation 267 to advance to the next pixel.

If the magnitude exceeds the threshold, then it is determined that the input image 106 does contain a sufficiently distinct edge at or near to the output point, and therefore the method 260 continues with operation 268.

Figure 14:
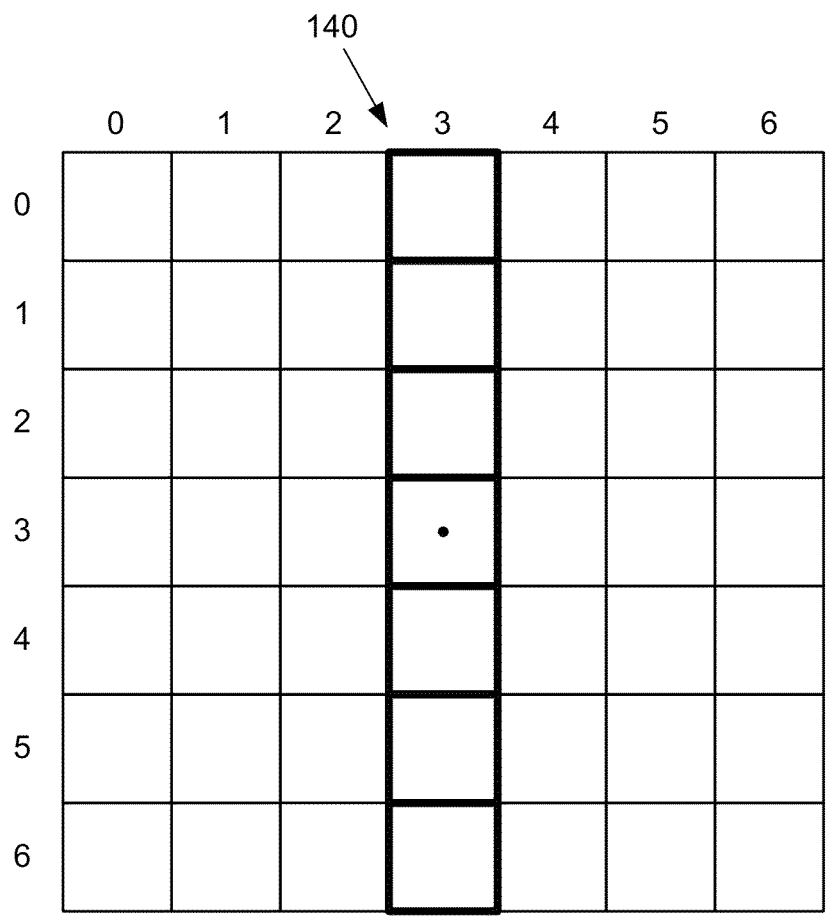
FIG. 14 is a schematic diagram illustrating an example of a line retrieved from the set of linear bisections shown in FIG. 6.

The operation 268 is performed to identify a line having the same angle as the retrieved angle for the analysis point. In some embodiments the line is retrieved from the set 138 of linear bisections, such as shown in FIG. 6. For example, if the retrieved angle is angle 0, the line 140 is retrieved. An example is illustrated in FIG. 14.

Some embodiments include an operation 270 that operates to shift the line position. Other embodiments do not include the operation 270, such that the method 260 proceeds directly to operation 272.

Figure 15:
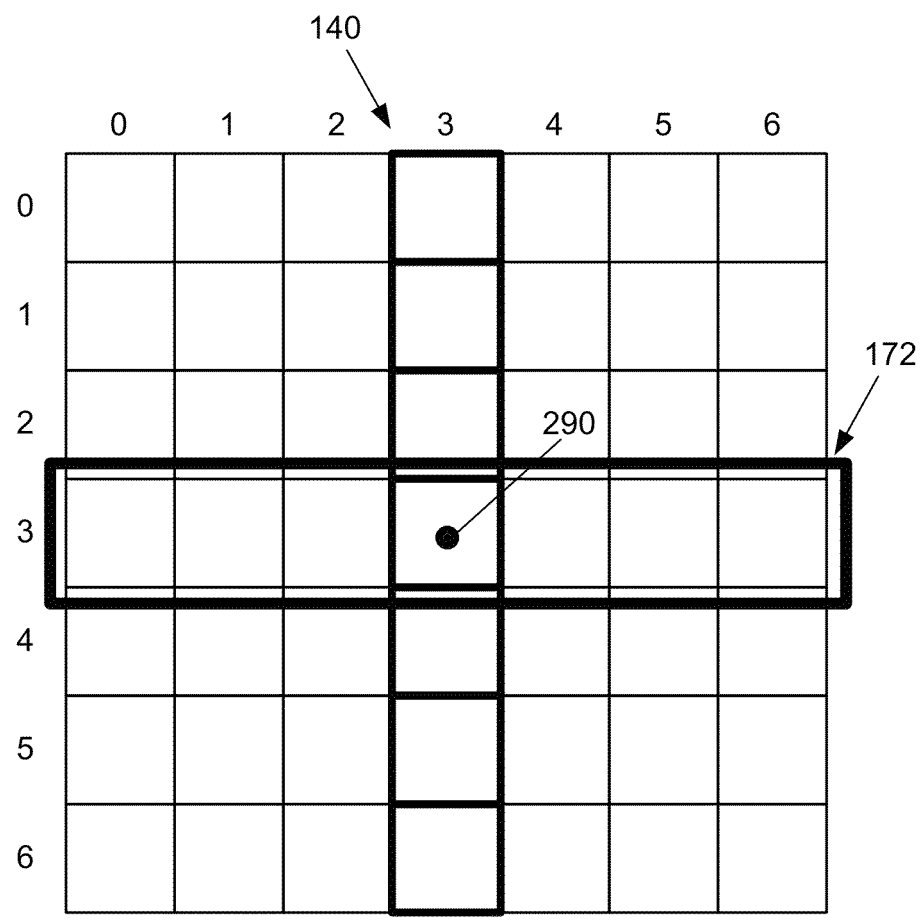
FIG. 15 is a schematic diagram illustrating an example of an operation to shift a line to an actual location of an edge in an input image.

Even though a significant difference between the intensity values may exist for the analysis point of the input image 106, the position of the edge in the image is not necessarily centered exactly at the analysis point. Therefore, in some embodiments the operation 270 is performed to shift the line position to the actual location of the edge in the input image. An example of operation 270 is illustrated in FIG. 15.

Figure 16:
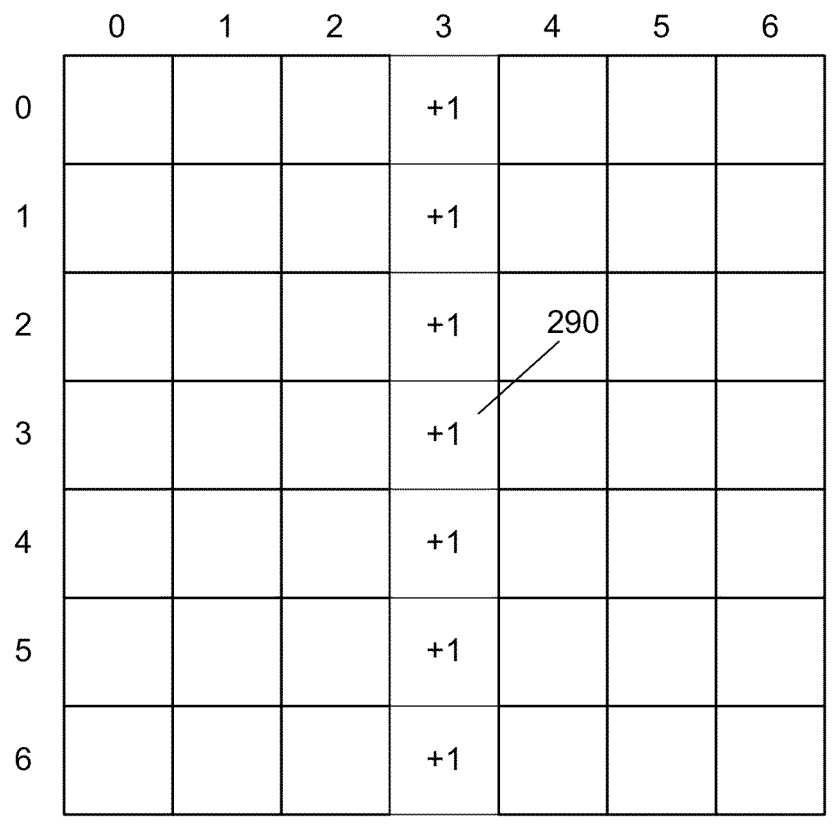

Once the appropriate location of the line has been determined, the operation 272 is performed to draw the line in the output image 108. An example of operation 272 is shown in FIG. 16.

The operation 274 is performed to determine whether additional pixels remain to be processed. If so, operation 276 is performed to set the next pixel as the output pixel and operations 264, 266, 268, 270, 272, and 274 are repeated accordingly.

FIG. 14 is a schematic diagram illustrating an example of the line 140 retrieved from the set 138 of linear bisections, such as shown in FIG. 6.

FIG. 15 is a schematic diagram illustrating an example of the operation 270, shown in FIG. 13, which is performed to shift a line 140 to the actual location of the edge in the input image.

In this example, after retrieving the line 140 from the set 138 of linear bisections, a second line is retrieved. The second line is the line perpendicular to the line 140. In this example, the line 172 (shown in FIG. 6) is perpendicular to the line 140, and therefore it is retrieved. The perpendicular line 172 is centered on the output point 290 of the output image 108.

The magnitude of each pixel corresponding to the perpendicular line 172 in the angle and magnitude map 250 is then evaluated to identify the pixel having the greatest magnitude. This pixel is determined to be the proper location of the edge in the input image 106. That pixel is then used in operation 272 as the center point for drawing the line 140 in the output image 108.

FIG. 16 is a schematic diagram illustrating an example of the operation 272, shown in FIG. 13, which is performed to draw a line in the output image 108.

In this example, the output point 290 is determined in operation 270 to have the greatest magnitude. Therefore, the operation 272 is performed to draw the line 140 in the output image 108. In some embodiments, drawing the line involves increasing the intensity value of the pixels corresponding to the line 140. In one example the intensity value is incremented by one.

Even though an increment of one may not be easily visually distinguishable to the human eye if the output image 108 is displayed on a display device, the intensity value can be read by a computing device to distinguish between a pixel having a value of 1 and another pixel having an intensity value of 2, for example. In some embodiments the output image 108 is not displayed, and instead is used for subsequent image processing by a computing device, such that it is not necessary for a human to be able to visually distinguish between different intensities. However, in other embodiments the intensity increments can be greater than one to permit differences in intensity values to be more easily visually distinguished by a human.

The line drawing process shown in FIG. 16 is then repeated for each additional pixel, as discussed with reference to FIG. 13, until all remaining pixels have been processed. The resulting lines drawn in the output image 108 identify the locations of the edges in the input image 106. An example of the output image 108 is shown in FIG. 1.

FIG. 17 is a perspective view of an example instrument 300 in which aspects of the present disclosure can be implemented.

One example of an instrument 300 is a medical instrument. A more specific example of a medical instrument is an ophthalmoscope, as shown.

In some embodiments the instrument 300 includes an image capture device 302. The image capture device 302 can be used to capture the input image 106, for example.

In some embodiments the instrument 300 includes a computing device 102. The computing device 102 includes the edge detection engine 104, such as illustrated and described herein. Accordingly, in some embodiments the operations of the edge detection engine are performed by the instrument 300.

In another embodiment, the computing device 102 and edge detection engine 104 can be separate from the instrument 300. For example, the image 106 captured by the instrument 300 is transferred to the computing device 102 by a wired, wireless, or combination of wired and wireless communication system.

In some embodiments the instrument 300 is configured for connection with a docking station through which the transmission of the image 106 to the computing device 102 can occur. The image 106 may also be physically transferred via a computer readable storage device in yet another possible embodiment.

Figure 18:
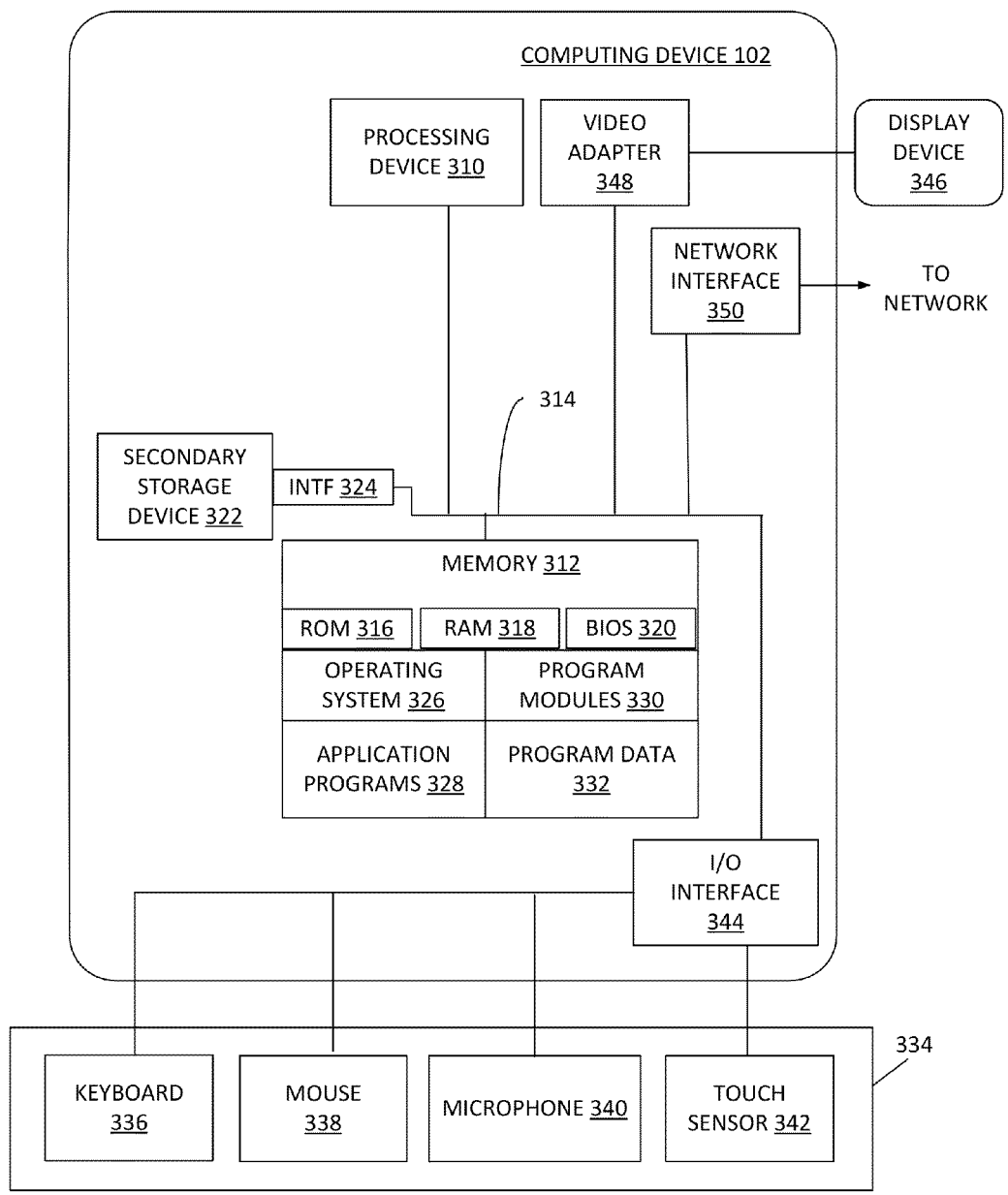
FIG. 18 illustrates an example of a computing device that can be used to implement aspects of the present disclosure.

FIG. 18 illustrates another example of the computing device 102 that can be used to implement aspects of the present disclosure. For example, the computing device 102 illustrated in FIG. 18 can be used to execute application programs and/or software modules (including the software engines) described herein.

The computing device 102 typically includes at least one processing device 310 and at least one computer readable medium.

One example of a processing device is a central processing unit (CPU). Other embodiments include other processing devices. For example, some embodiments include a graphics processing unit (GPU). Other embodiments include compute unified device architecture (CUDA) cores or other single instruction multiple data (SIMD) devices that can assign resources to process pixels in parallel, which may be up to hundreds of times faster than a typical CPU. Yet other embodiments include a programmable gate array (PGA), complex programmable logic device (CPLDs), system on chip (SoCs), or application-specific integrated circuits (ASICs), for example.

The computing device 102 also typically includes at least some form of computer readable media. Computer readable media includes any available media that can be accessed by the computing device 102. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 102. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Some embodiments include two or more computing devices. For example, a first computing device can be used for image acquisition, while another computing device is used for image processing. As another example, two or more computing devices can be used for image processing. Further, in some embodiments a single computing device includes multiple processors and multiple computer readable media, which may be remote from each other. Communication between the multiple components of one or more computing devices can occur across one or more communication networks, for example. Data can be transferred using one or more of a shared memory bus, Ethernet, Bluetooth, WiFi, or other data communication networks, for example.

In the illustrated example, the computing device 102 also includes a system memory 312, and a system bus 314 that couples various system components including the system memory 312 to the processing device 310. The system bus 314 is one of any number of types of bus structures including a memory bus, or memory controller; a peripheral bus; and a local bus using any of a variety of bus architectures.

Examples of computing devices suitable for the computing device 102 include a server, a desktop computer, a laptop computer, a tablet computer, a mobile computing device (such as a smart phone, an iPod® or iPad® mobile digital device, or other mobile devices), or other devices configured to process digital instructions.

In some embodiments the system memory 312 includes read only memory 316 and random access memory 318. A basic input/output system 320 containing the basic routines that act to transfer information within computing device 102, such as during start up, is typically stored in the read only memory 316.

In the illustrated example the computing device 102 also includes a secondary storage device 322, such as a hard disk drive, for storing digital data. The secondary storage device 322 is connected to the system bus 314 by a secondary storage interface 324. The secondary storage devices 322 and their associated computer readable media provide nonvolatile storage of computer readable instructions (including application programs and program engines or modules), data structures, and other data for the computing device 102.

Although the exemplary environment illustrated in FIG. 18 employs a hard disk drive as a secondary storage device 322, other types of computer readable storage media are used in other embodiments. Examples of these other types of computer readable storage media include flash memory cards, compact disc read only memories, random access memories, or read only memories. Some embodiments include non-transitory media. Additionally, such computer readable storage media can include local storage or cloud-based storage.

A number of program modules can be stored in a secondary storage device 322 or memory 312, including an operating system 326, one or more application programs 328, other program modules 330 (such as the software engines described herein), and program data 332. The computing device 102 can utilize any suitable operating system, such as Microsoft Windows™, Google Chrome™, Apple OS, and any other operating system suitable for a computing device.

In some embodiments, a user provides inputs to the computing device 102 through one or more input devices 334. Examples of input devices 334 include a keyboard 336, mouse 338, microphone 340, and touch sensor 342 (such as a touchpad or touch sensitive display). Other embodiments include other input devices 334. The input devices are often connected to the processing device 310 through an input/output interface 344 that is coupled to the system bus 314. These input devices 334 can be connected by any number of input/output interfaces, such as a parallel port, serial port, game port, or a universal serial bus. Wireless communication between input devices and the interface 344 is possible as well, and includes infrared, BLUETOOTH® wireless technology, 802.11a/b/g/n, cellular, or other radio frequency communication systems in some possible embodiments.

In this example embodiment, a display device 346, such as a monitor, liquid crystal display device, projector, or touch sensitive display device, is also connected to the system bus 314 via an interface, such as a video adapter 348. In addition to the display device 346, the computing device 102 can include various other peripheral devices (not shown), such as speakers or a printer.

When used in a local area networking environment or a wide area networking environment (such as the Internet), the computing device 102 is typically connected to a communication network through a network interface 350, such as an Ethernet interface. Other possible embodiments use other communication devices. For example, some embodiments of the computing device 102 include a modem for communicating across the network.

The computing device illustrated in FIG. 18 is also an example of programmable electronics, which may include one or more such computing devices, and when multiple computing devices are included, such computing devices can be coupled together with a suitable data communication network so as to collectively perform the various functions, methods, or operations disclosed herein.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method of detecting edges within a digital image, the method comprising:
   processing at least a portion of the digital image, using a computing device, in a pixel-by-pixel manner including at an analysis point in the digital image, by:
   identifying pixels surrounding the analysis point;
   identifying a location of a bisection that divides the pixels surrounding the analysis point into two halves;
   determining an angle of the bisection that maximizes a difference in intensities of the pixels between the two halves;
   determining that an edge is present in the digital image at the angle of the bisection; and
   moving the analysis point sequentially across the pixels of at least a portion of the digital image and repeating the processing.

2. The method of claim 1, wherein identifying pixels surrounding the analysis point involves the use of an annular aperture mask.

3. The method of claim 2, wherein the annular aperture mask is generated using a circle drawing algorithm.

4. The method of claim 1, wherein determining that an edge is present in the digital image comprises determining whether the difference in intensities between the two halves is greater than a threshold.

5. The method of claim 1, further comprising generating an angle and magnitude map and storing the angle of the bisection and a magnitude of the difference in intensities of the pixels between the two halves in the angle and magnitude map for the analysis point.

6. The method of claim 1, further comprising generating an output image after determining that an edge is present in the digital image.

7. The method of claim 6, wherein generating output data comprises drawing a line in the output image at the angle of the bisection.

8. The method of claim 7, further comprising:
   checking a set of pixels perpendicular to the bisection before drawing the line to determine a point of greatest magnitude; and
   shifting a position of the line to the point of greatest magnitude.

9. An edge detection system comprising:
   a computing device comprising:
   a processing device; and
   a computer readable storage device storing data instructions that, when executed by the processing device generates an edge detection engine comprising:
   an annular aperture generator that operates to generate an annular aperture using a circle drawing algorithm;
   a line generator that generates lines representative of a set of bisectors of the annular aperture, wherein the line generator generates lines representative of the set of all possible bisectors of the annular aperture;
   an image scanning engine that utilizes the annular aperture as a mask to scan a digital image and identify edges within the digital image; and
   an output data generator that utilizes the lines to represent the edges in the output image.

10. The computing device of claim 9, wherein the circle drawing algorithm is Bresenham's circle algorithm.

11. The computing device of claim 9, wherein the annular aperture has a thickness of one pixel.

12. The computing device of claim 9, wherein the annular aperture has a radius in a range from about 5 pixels to about 25 pixels.

13. The computing device of claim 9, wherein the line generator utilizes Bresenham's line algorithm.

14. The computing device of claim 9, wherein the image scanning engine generates an angle and magnitude map identifying an angle and a magnitude for potential edge identified in the digital image.

15. A medical instrument comprising:
- an image capture device operable to capture an input image; and
- a computing device including an edge detection engine, the edge detection engine operable to process the input image to detect edges within the input image by processing the image using an annular aperture mask, the edge detection engine being further operable to:
- identify pixels surrounding an analysis point;
- identify a location of a bisection that divides the pixels surrounding the analysis point into two halves:
- determine an angle of the bisection that maximizes a difference in intensities of the pixels between the two halves; and
- determine that an edge is present in the digital image at the angle of the bisection.

16. The medical instrument of claim 15, wherein the medical instrument is an ophthalmoscope.

17. The medical instrument of claim 15, wherein the medical instrument is a culposcope.

* * * * *